United States Patent
MacCormick et al.

(10) Patent No.: US 11,633,484 B2
(45) Date of Patent: Apr. 25, 2023

(54) METHOD FOR IMPROVING THE ORAL BIOAVAILABILITY OF A DRUG

(71) Applicant: PharmaCytics B.V., Nijmegen (NL)

(72) Inventors: Somhairle MacCormick, Nijmegen (NL); Gerrit Herman Veeneman, Nijmegen (NL)

(73) Assignee: PharmaCytics B.V., Nijmegen (NL)

( * ) Notice: Subject to any disclaimer, the term of this patent is extended or adjusted under 35 U.S.C. 154(b) by 0 days.

(21) Appl. No.: 16/956,172

(22) PCT Filed: Dec. 18, 2018

(86) PCT No.: PCT/EP2018/085567
§ 371 (c)(1),
(2) Date: Jun. 19, 2020

(87) PCT Pub. No.: WO2019/121734
PCT Pub. Date: Jun. 27, 2019

(65) Prior Publication Data
US 2020/0330602 A1   Oct. 22, 2020

(30) Foreign Application Priority Data
Dec. 21, 2017 (EP) .................................. 17209734

(51) Int. Cl.
*A61K 47/54* (2017.01)
*C07H 15/18* (2006.01)
*C07H 15/26* (2006.01)
*C07H 19/067* (2006.01)

(52) U.S. Cl.
CPC ........... *A61K 47/549* (2017.08); *C07H 15/18* (2013.01); *C07H 15/26* (2013.01); *C07H 19/067* (2013.01)

(58) Field of Classification Search
CPC ............ A61K 47/549; C07H 15/18–26; C07H 19/00–24
See application file for complete search history.

(56) References Cited

U.S. PATENT DOCUMENTS

| | | |
|---|---|---|
| 5,955,100 A | 9/1999 | Bosslet et al. |
| 2012/0065152 A1 | 3/2012 | Whomsley et al. |
| 2012/0264702 A1 | 10/2012 | Shull et al. |
| 2016/0303254 A1* | 10/2016 | Kolakowski ............ A61P 37/06 |

FOREIGN PATENT DOCUMENTS

| | | | |
|---|---|---|---|
| EP | 2 098 533 | 9/2009 | |
| WO | WO-2017053574 A1 * | 3/2017 | ........... C07H 15/203 |

OTHER PUBLICATIONS

Walther, R. et al "Prodrugs in medicinal chemistry . . . " Adv. Drug Rev., vol. 118, pp. 65-77. (Year: 2017).*
Madec-Laugerstay, R. et al "Synthesis of self-immolative glucuronide spacers . . . " J. Chem. Soc., Perkin Trans. 1, pp. 1369-1375. (Year: 1999).*
International Search Report & Written Opinion, International Patent Application No. PCT/EP2018/085567, dated Feb. 4, 2019, 8 pages.

* cited by examiner

*Primary Examiner* — Leigh C Maier
(74) *Attorney, Agent, or Firm* — Casimir Jones, SC; Robert A. Goetz

(57) ABSTRACT

The invention is in the field of medical sciences. It provides new pharmaceutical methods and preparations. In particular, the invention relates to a method for increasing the oral bioavailability of drugs. The invention also provides new compositions comprising a drug covalently attached to a saccharide as in formula (I) below. More in particular, the invention relates to a method for increasing the oral bioavailability of a drug by covalently attaching a sugar-linked, N-substituted or unsubstituted carbamoylalkylidene moiety to a hydroxyl or thiol group of a drug, wherein the substituents are as defined in the claims.

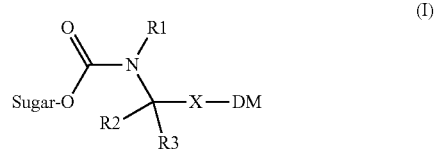

(I)

8 Claims, No Drawings

METHOD FOR IMPROVING THE ORAL BIOAVAILABILITY OF A DRUG

The present invention relates to new compounds, in particular compounds that are prodrugs and that can enhance the oral availability of known and future drugs. The invention also relates to a method for increasing the oral availability of drugs by linking the drug to a sugar-carbamoyl-alkylidene unit to obtain the compound of the invention.

Oral administration is among the most preferred routes to deliver medication to patients. However, inadequate oral bioavailability is a significant problem in the pharmaceutical world. Low oral bioavailability is associated with a lower efficacy and a variable patient response [Hellriegel, E. T., *Clin. Pharmacol. Ther.*, 1996, 60, 601-7]. Drugs expressing low oral bioavailability are more difficult and also more costly to transform into an acceptable formulation.

To compensate for low oral bioavailability a higher dose is generally required to realize the intended therapeutic effect, but a higher dose may also lead to a higher burden of dose-related side-effects, particularly in the intestinal tract. In addition, a drug showing low oral bioavailability has a lower potential to be repositioned for new indications. Furthermore, several drug products are currently only available as injectable formulations and there is a great need for technologies that can facilitate reformulation of those drugs into effective oral applications.

Analysis of a large number of marketed drugs according to the Biopharmaceutics Drug Disposition Classification System (BDDCS) [Benet, L. Z., *AAPS J.*, 2011, 13, 519-47] revealed that 40% of the marketed drugs show poor solubility (Class 2 and 4 drugs) whereas 30% of the drugs show poor permeability as indicated by their poor metabolism (Class 3 and 4 drugs). It was further estimated that, from the drug candidates being investigated by the industry, up to 70% are poorly soluble class 2 compounds, while another 20% are not only poorly soluble but also poorly permeable and belong to class 4 compounds. It may therefore be concluded that the design of new chemical entities showing adequate oral bioavailability is becoming increasingly difficult.

The problem of poor oral bioavailability may be attributable to a number of causes. Firstly it is known that many oral drugs are hydrophobic and therefore poorly soluble. Secondly, many drugs show insufficient membrane permeability in the gastrointestinal tract. Also, many drugs are sensitive to metabolism by intestinal and/or hepatic enzymes before they reach their target site of action. In addition, certain drugs may be actively pumped out from the enterocytes by efflux transporters before entering the blood circulation.

Many remedies have been proposed to solve the problem of unsatisfactory oral bioavailability of drugs [Fasinu, P., *Biopharm Drug Disp.*, 2011, 32, 185-209]. Proposed strategies include for instance solubilisation technologies, such as the use of different salts, reduction of the particle size, e.g. by micronisation or nanonisation, the use of spray-dried dispersions and hot melt extrusion as well as the use of lipophilic liquids and semi-solid matrixes. None of these strategies appears universally applicable to resolve oral bioavailability problems and each time their potential need to be investigated on a case by case basis.

Another strategy to enhance drug oral bioavailability is the use of prodrugs [*Prodrugs and Targeted Delivery*, Rautio, J, (Ed.), 2011, Wiley-VCH, Weinheim, Germany]. Prodrugs can conceptually be divided into two categories, bioprecursor prodrugs and carrier prodrugs [*The Practice of Medicinal Chemistry*, Ch. 31-32, Ed. Wermuth, Academic Press, San Diego, Calif., 2008]. Generally, bioprecursor prodrugs are compounds that are inactive or have low activity compared to the corresponding parent drug compound, but can be converted to the parent drug by metabolism or hydrolysis.

Carrier prodrugs are drug compounds that contain a promoiety, i.e. a covalently bound molecule that transiently corrects a specific suboptimal physicochemical property of a drug candidate. Such carrier prodrugs are often advantageous for orally administered drugs.

A special subset of carrier prodrugs are drug-glycosides, in which the anomeric hydroxyl group of a sugar moiety is covalently linked to a drug molecule. Several reports have demonstrated the usefulness of drug-glycosides to improve the physicochemical properties of a drug but evidence that drug-glycosides can enhance the oral bioavailability of a drug remain scarce.

Improved transport of β-D-gluco-pyranoside (β-D-glucoside) and β-D-galactopyranoside (β-D-galactoside) conjugates of small phenolic compounds such as p-nitrophenol and 1- or 2-naphthol through the intestinal membrane was reported. The absorption rate of the β-D-glucose conjugate was found to be higher than that of the β-D-galactose conjugate [Biochim. Biophys. Acta, 1994, 1200, 117].

Oral application of prednisolone-21-O-β-D-glucoside in rat was disclosed to produce a two-fold increase of serum levels with respect to prednisolone [US 2001/0041676]. WO 2003/073988 discloses the preparation of glycuronamide and glycoside prodrugs of fluoxetine. No evidence of improved oral bioavailability is presented.

Oral administration of a β-O-glucoside prodrug of 7-hydroxy-3-methoxy cadalene was found to reduce tumor volume by 50% in a xenograft mouse model, whereas 7-hydroxy-3-methoxy cadalene itself did not show tumor volume reduction. The effect was attributed to a better solubility of the glucoside. No pharmacokinetic data on oral bioavailability were provided [Bioorg. Med. Chem. Lett., 2007, 7, 6335].

Glycosylated analogs of acetaminophen [US 2012/0022012] showed improved solubility but strongly reduced oral bioavailability with respect to acetaminophen.

US 2012/0264702 describes glycosylated analogs of propofol. These compounds appear to show improved water solubility for intravenous administration. However, none of the compounds shown leads to a significantly enhanced propofol concentration. No data for improvement of oral bioavailability are presented.

EP2098533 describes a glucuronic acid prodrug of doxorubicin, The glucuronic acid is attached to doxorubicin through an 4-aminobenzyl-carbamate linker.

The goal is to deliver the doxorubicin at a higher level to the tumor. No data on oral bioavailability are presented.

In U.S. Pat. No. 5,955,100 glycoside prodrugs are claimed to be less toxic compared to the parent drug and to accumulate more efficiently in tumor cells, compared to the parent drugs. In this case glucuronic acid was attached through a 4-hydroxybenzyl linker to drugs, such as doxorubicin, quinine and reserpine. The glycoconjugates are administered intravenously. No data on oral bioavailability are disclosed.

US2012/0065152A discloses a methyl 6-O-carbamoyl-β-D-glucoside prodrug linked to the amidine moiety of guanfacine. Oral administration of the prodrug in a pharmacokinetic study in rat gave a lower value of the relative $C_{max}$ compared to guanfacine itself, suggesting a lower oral bioavailability.

An ex-vivo study with benzyl β-D-glucopyranoside revealed that intestinal carrier-mediated transport across the brush border membrane improves the intestinal availability of nutritionally, pharmacologically or physiologically active compounds that undergo intestinal metabolism [Biochim. Biophys. Acta, 2005, 1722, 218].

On the other hand, several reports indicate that intestinal absorption and hydrolysis of the O-glucosides to the parent drug does not occur readily. For example, nearly 60% of an orally administered dexamethasone glucoside reached the caecum as a free steroid, while orally administered parent steroids were absorbed almost exclusively from the small intestine [J. Med. Chem., 1984, 27, 261].

Despite those many endeavours with glycoconjugates of drugs to enhance physicochemical properties, there remains a need for improved methods to increase the oral bioavailability of a drug.

It has now been found that the oral bioavailability of a hydroxyl or thiol containing drug can be improved by covalently attaching a glycosyl carbamoylalkylidene unit as described below to a hydroxyl or thiol containing drug moiety.

The invention thus provides a compound of formula (I)

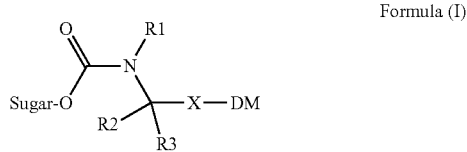

Formula (I)

wherein
Sugar is selected from the group consisting of alpha- and beta-linked monosaccharides and disaccharides, wherein optionally one or more OH groups are replaced by a group R4;
wherein R4 is selected from the group consisting of $C_1$-$C_6$ alkoxy, chlorine, fluorine, cyano, $OF_3$, $NH_2$, $C_1$-$C_6$ alkyl-NH, $C_1$-$C_6$ dialkyl-N, $C_1$-$C_6$ cycloalkyl-N, $C_1$-$C_6$ alkyl-C(O)NH, $C_1$-$C_6$ alkyl-C(O)($C_1$-$C_6$ alkyl)-N, HC(O)($C_1$-$C_6$ alkyl)-N, $C_1$-$C_6$ alkyl-O—C(O)NH, $C_1$-$C_6$ alkyl-O—C(O)($C_1$-$C_6$ alkyl)—N, and $C_1$-$C_6$ alkyl-O—C(O)—O;
R1 is selected from the group consisting of H, $C_1$-$C_6$ alkyl, $C_2$-$C_6$ alkenyl, $C_2$-$C_6$ alkynyl, —R5—O—R7, —R5—S—R7, —R6—C(O)—R7, —R6—C(O)—O—R7, —R5—$SO_2$—R7, —R5—$SO_2$—NR7R8, $C_3$-$C_7$ cycloalkyl, $C_4$-$C_7$ cycloalkenyl, a 4 to 7 membered heterocycle, aryl and ($C_1$-$C_3$ alkyl)-aryl;
wherein R5 is $C_2$ or $C_3$ alkyl, R6 is $C_1$-$C_3$ alkyl, R7 and R8 are independently hydrogen or $C_1$-$C_3$-alkyl;
and wherein the $C_3$-$C_7$ cycloalkyl, $C_4$-$C_7$ cycloalkenyl, a 4 to 7 membered heterocycle, aryl and ($C_1$-$C_3$ alkyl)-aryl groups can be optionally substituted by R9,
wherein R9 is selected from the group consisting of $C_1$-$C_4$ alkyl, $C_1$-$C_4$ alkoxy, chlorine, fluorine, cyano, $CF_3$, amine, amide, carbamate and —C(O)O—($C_1$-$C_4$-alkyl);
R2 and R3 are both H, or one of R2 and R3 is H and the other is $C_1$-$C_6$ alkyl;
X-DM represents a drug moiety, wherein X is O or S;
or a pharmaceutically acceptable salt thereof.

The present invention as defined above provides the advantage of improving the oral bioavailability of a drug.

In the above definitions, "alkyl" can be branched or unbranched.

Examples of alkyl include methyl, ethyl, n-propyl, i-propyl, n-butyl, i-butyl, sec-butyl, t-butyl and n-pentyl.

"Alkoxy" refers to an alkyl group bonded to oxygen. Examples of alkoxy include methoxy, ethoxy and propoxy.

"Alkenyl" refers to a branched or unbranched hydrocarbon residue having at least one carbon to carbon double bond. Examples of alkenyl include ethenyl (vinyl), allyl, prop-1-enyl, but-1-enyl, but-2-enyl, but-3-enyl, 2-methylprop-2-enyl, pentenyl and hexenyl.

"Alkynyl" refers to a hydrocarbon residue having at least one carbon to carbon triple bond. Examples of alkynyl include ethynyl, propynyl, butynyl and pentynyl.

"Cyano" refers to the group —CN.
"Amino" refers to the group —$NH_2$.
"Amide" refers to the group —C(O)$NH_2$.
"Carbamate" refers to a group —NH—C(O)—O—
"Cycloalkyl" refers to a saturated hydrocarbon ring. Examples of cycloalkyl include cyclopropyl, cyclobutyl, cyclopentyl, cyclohexyl and cycloheptyl.

"Cycloalkenyl" refers to a partially saturated hydrocarbon ring. Examples of cycloalkenyl include cyclobutenyl, cyclopentenyl and cyclohexenyl.

"Heterocycle" refers to an aromatic, saturated or partially saturated ring structure having 3 to 6 carbon atoms and 1 or 2 hetero atoms selected from nitrogen, sulfur and oxygen. Examples of heterocycle include thienyl, furyl, pyranyl, pyrrolyl, imidazolyl, pyrazolyl, isothiazolyl, isoxazolyl, pyridyl, pyrazinyl, pyrimidinyl, pyridazinyl, oxetanyl, tetrahydrofuranyl, tetrahydropyranyl, pyrrolinyl, piperidinyl and morpholinyl.

"Aryl" refers to an aromatic hydrocarbon ring. Examples of aryl include phenyl and naphtyl.

With "drug" is meant a pharmaceutically active agent. This can be an approved drug of medicament, or a candidate drug undergoing laboratory testing, preclinical or clinical trials.

As described above "Sugar" refers to alpha- and beta-linked monosaccharides and disaccharides. Monosaccharides have the general molecular formula $(CH_2O)_n$, where n can be 4, 5 or 6. They can be classified according to the number of carbon atoms in a molecule. Monosaccharides where n is 4 are referred to as tetroses, where n is 5, these are referred to as pentoses, e.g. ribose and deoxyribose, and where n is 6, these are referred to as hexoses, e.g. mannose, glucose and galactose.

Disaccharides are made up of two monosaccharide units. Examples of relevant disaccharides are maltose, isomaltose, cellobiose, gentiobiose and lactose.

Preferably Sugar is an alpha- or beta-linked monosaccharide or disaccharide. More preferably Sugar is a hexose or a pentose. The hexose is preferably selected from the group consisting of a glucose, galactose, mannose, or their partially deoxygenated or substitution variants. Most preferably the hexose is glucose or galactose.

With partially deoxygenated monosaccharide is meant C-2, C-4 or C-6 deoxy variants.

The monosaccharide can have either an alpha or beta linkage in the compound of formula (I).

An example thereof is

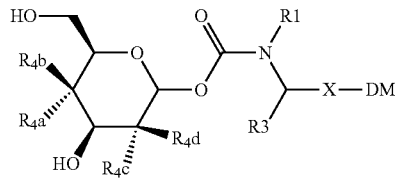

Most preferred sugar is β-glucose or β-galactose.

Preferred groups for R1 are H, $C_1$-$C_4$ alkyl, $C_1$-$C_4$ alkenyl, —R5—O—R7, —R5—S—R7, —R6—C(O)—R7, —R6—C(O)—O—R7, —R5—$SO_2$—R7, —R5—$SO_2$—NR7R8, $C_3$-$C_7$ cycloalkyl, wherein $C_3$-$C_7$ cycloalkyl is optionally substituted by one or two fluorine; pyranyl, tetrahydrofuranyl and benzyl, wherein R5 is $C_2$ or $C_3$ alkyl, R6 is $C_1$-$C_3$ alkyl, R7 and R8 are independently hydrogen or $C_1$-$C_3$ -alkyl.

R1 is most preferably selected from the group consisting of H; $C_1$-$C_4$ alkyl, in particular methyl, ethyl, propyl, isopropyl and butyl; allyl; methoxyethyl, in particular 2-methoxyethyl; ethoxyethyl, in particular 2-ethoxyethyl; methylthioethyl, in particular 2-methylthioethyl; $C_3$-$C_6$ cycloalkyl, optionally substituted by one or two F, in particular cyclopropyl, cyclobutyl, 3,3-difluorocyclobutyl, cyclopentyl and cyclohexyl; pyranyl, in particular 4-pyranyl; tetrahydrofuranyl, in particular 3-R-THF or 3—S-THF; benzyl; carbethoxymethyl; carbomethoxyethyl and methanesulfonylethyl, in particular 2-methanesulfonylethyl.

R2 and R3 are preferably both H, or one of R2 and R3 is H and the other is methyl. Most preferably R2 and R3 are both H.

As described above, in the Sugar optionally one or more OH groups can be replaced by a group R4. Preferably no OH groups are replaced or one or two OH groups are replaced by fluorine (F).

Thus a preferred compound of the invention is a compound having the structure

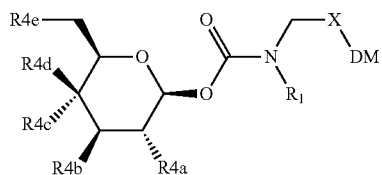

wherein R1 is as defined above. R4a, R4b, R4c, R4d and R4e are independently selected from OH, F and H with the following provisions: at least two of R4a, R4b, R4c, R4d and R4e are OH whereas R4c and R4d cannot both be OH.

Examples of such preferred compounds are:

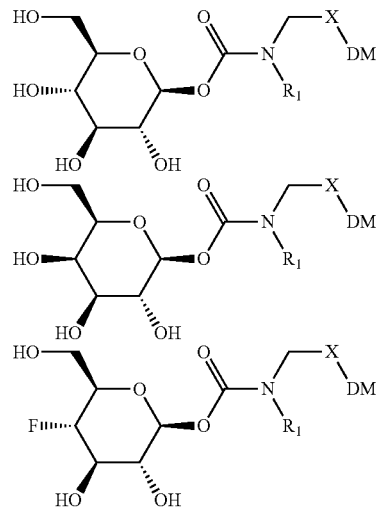

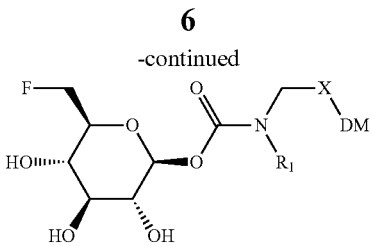

The drug moiety X-DM is the residue of the drug HX-DM, wherein HX represents a functional OH or SH group, after coupling to the carbamoylakylidene unit of the invention.

In a preferred embodiment the drug is selected from compounds containing at least three carbon atoms, having a molecular weight between 100 and 800 Daltons, the number of rotatable bonds being less than 15, being devoid of charged moieties such as phosphates and sulfates and having 1 to 3, preferably not more than 2, aliphatic and/or aromatic hydroxyl groups.

Examples of such drug moieties are:

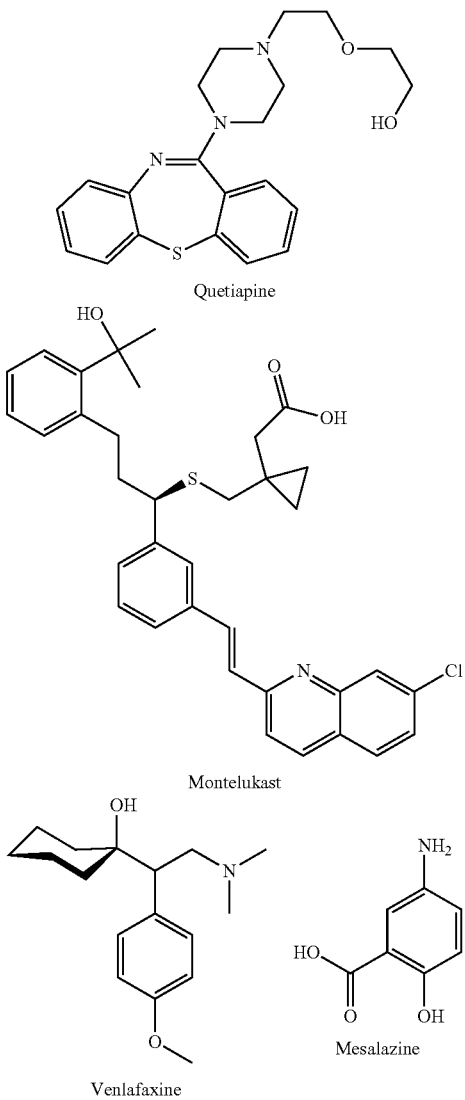

7
-continued
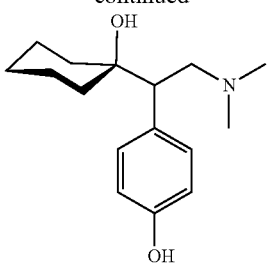
Desvenlafaxine
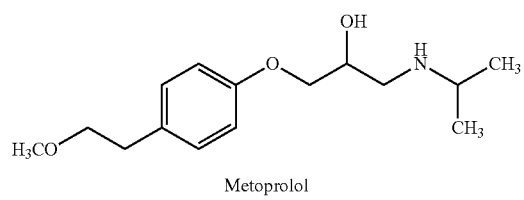
Metoprolol
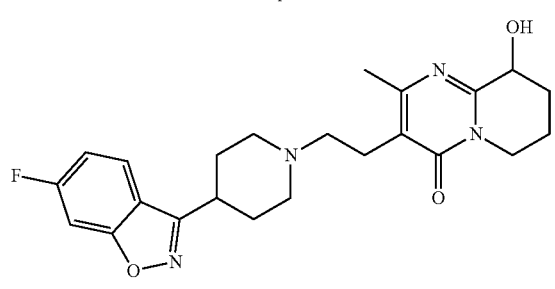
Paliperidone
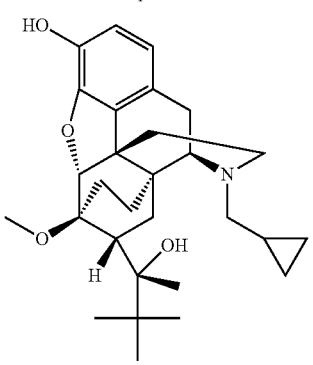
Buprenorphine
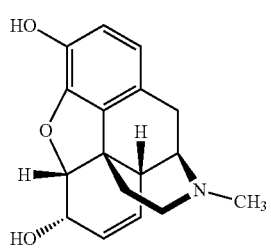
Morphine
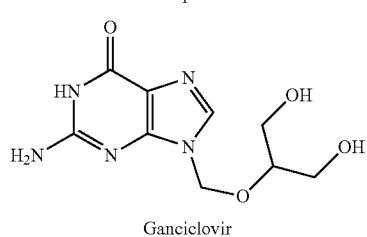
Ganciclovir
8
-continued
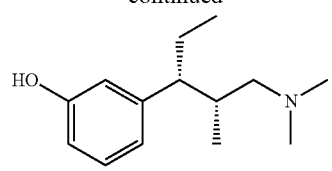
Tapentadol
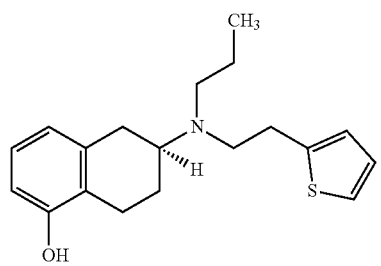
Rotigotine
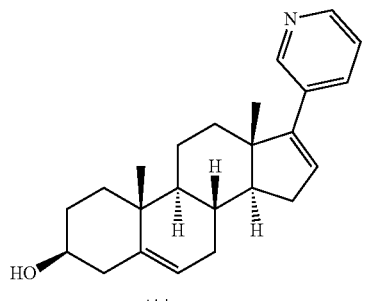
Abiraterone
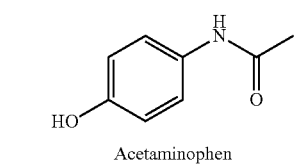
Acetaminophen
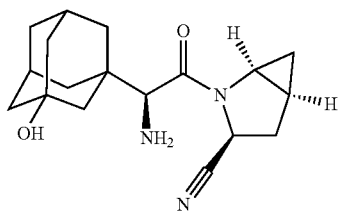
Saxagliptin
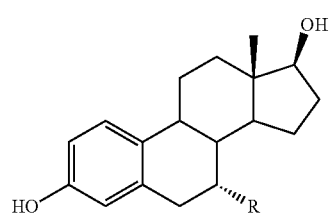
R = —$(CH_2)_9SO(CH_2)_3CF_2CF_3$
Fulvestrant -continued
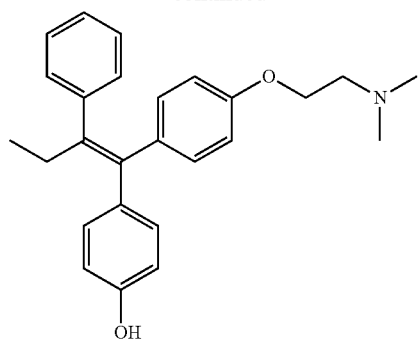
Afimoxifene
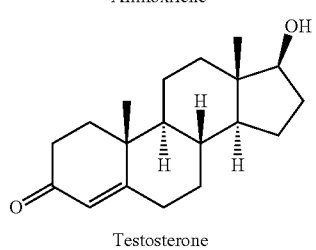
Testosterone
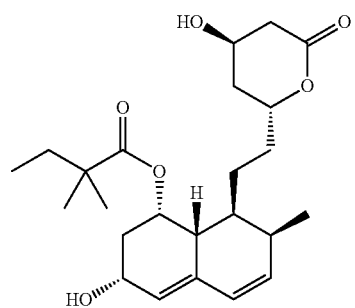
Simvastatin
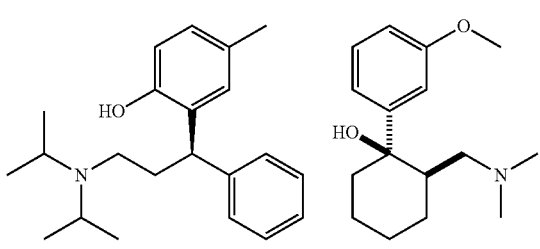
Tolterodine    Tramadol
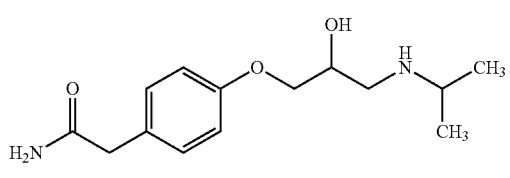
Atenolol
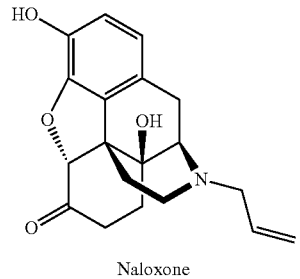
Naloxone
-continued
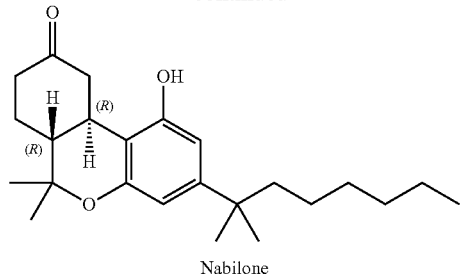
Nabilone
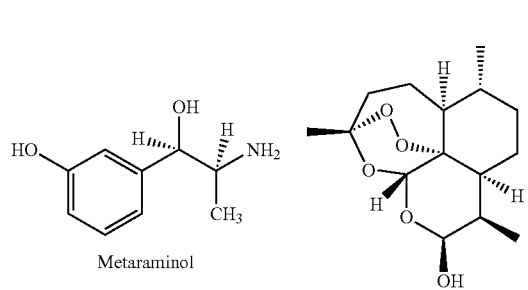
Metaraminol    Dihydroartemisin
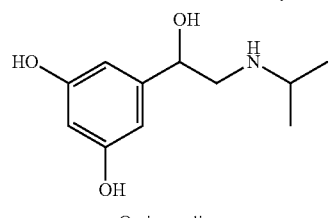
Orciprenaline
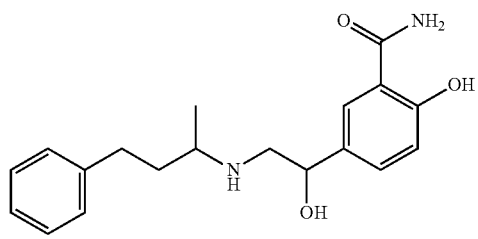
Labetalol
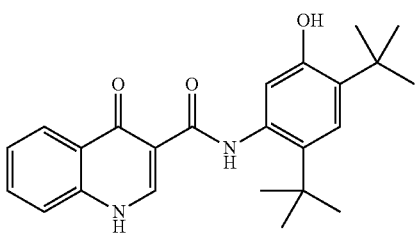
Kalydeco
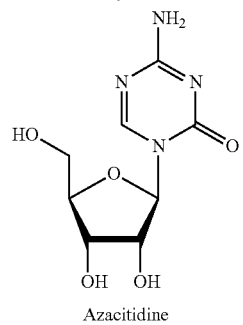
Azacitidine -continued

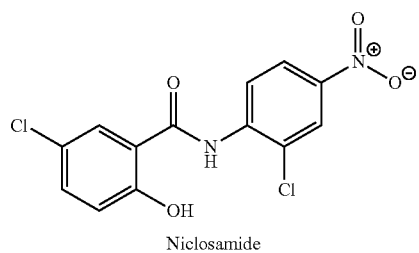
Niclosamide

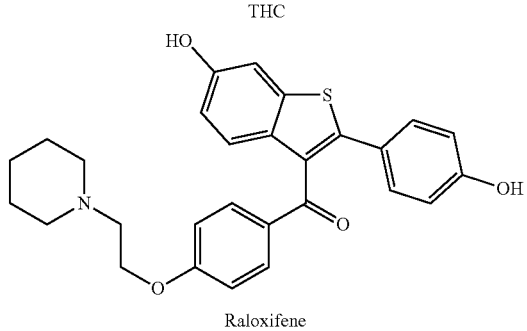
THC

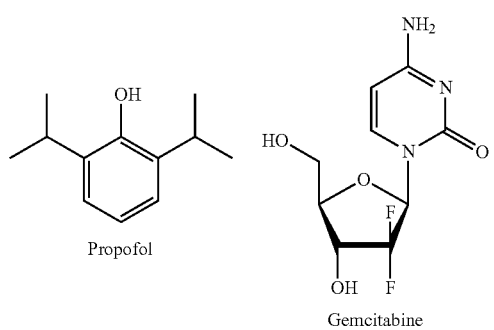
Raloxifene

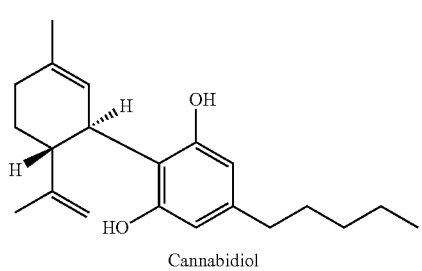
Propofol

Gemcitabine

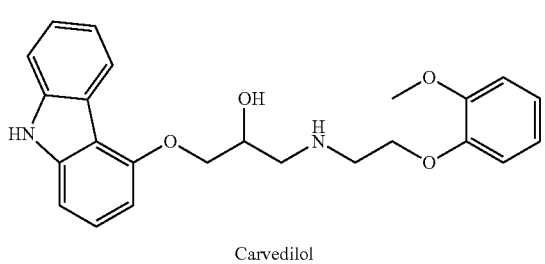
Cannabidiol

Carvedilol

-continued

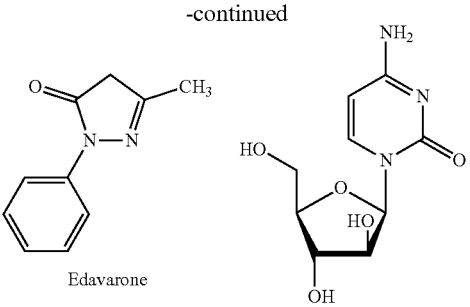
Edavarone

Cytarabine

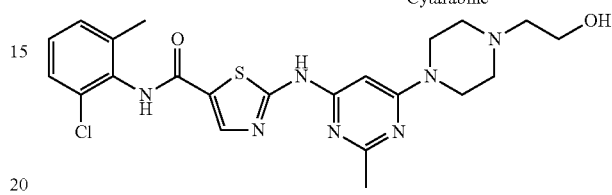
Dasatinib

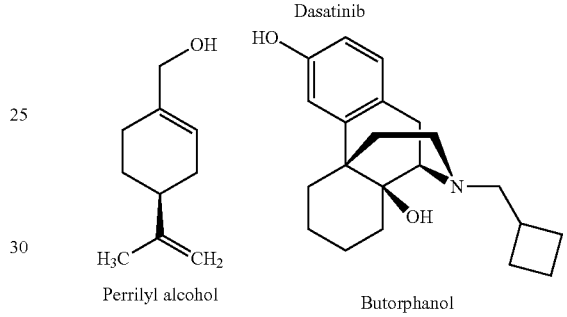
Perrilyl alcohol

Butorphanol

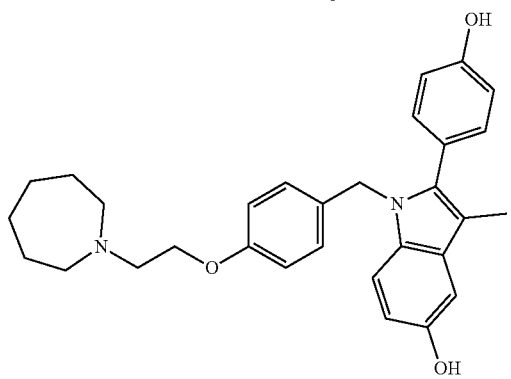
Bazedoxifene

Specific examples of drugs that can be advantageously used in the present invention are Abiraterone, Kalydeco, Niclosamide, Dihydroartemisinin, Gemcitabine, Cannabidiol, Dasatinib, Rotigotine, Edavarone and Fulvestrant.

The present invention is not only suitable for improvement of the oral bioavailability of existing drugs but can also be used for future drugs and drug candidates. It offers a platform for generally improving oral bioavailability.

The present invention further relates to a compound of Formula (I) as described above for use as a medicament.

The present invention also relates to a method of treating a disorder wherein the compound of Formula (I) as described above is administered to a subject in need of treatment or the disorder.

Treatment as mentioned herein is also meant to include mitigation or prevention of a disorder.

The disorder to be treated will depend on the drug used in the compound of Formula (I). This knowledge is available to the person skilled in the art.

The invention further provides a method for increasing the oral bioavailability of a drug HX-DM. wherein HX represents an OH or SH functional group, comprising the step of linking a sugar-carbamoylalkylidene unit of formula (II)

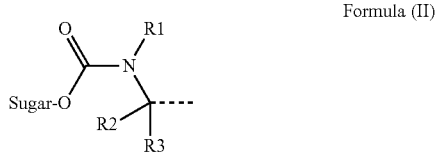

Formula (II)

wherein Sugar, R1, R2 and R3 are as defined above and ----- wherein represents a leaving group,
to the OH or SH functional group of the drug HX-DM in order to obtain a compound according to formula (I)

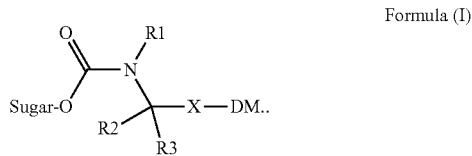

Formula (I)

With "leaving group" is meant a group such as Cl that is present in the initial sugar-carbamoylalkylidene unit of Formula (II) but no longer present in the final compound of Formula (I).

The term "oral bioavailability" refers to the extent and rate at which the drug enters the systemic circulation after oral administration, thereby becoming available to access the site of desired action.

Oral bioavailability is usually assessed by determining the area under the plasma concentration—time curve (AUC) [ADMET for medicinal chemists, Tsaioun, K. and Kates, S. A. (Eds.), 2011, Ch. 5, Wiley]).

Plasma drug concentration increases with extent of absorption; the peak concentration is reached when drug elimination rate equals absorption rate. Peak time is the most widely used general index of absorption rate; the slower the absorption, the later the peak time.

The most reliable measure of a drug's oral bioavailability is AUC. The AUC is directly proportional to the total amount of unchanged drug that reaches systemic circulation. Drug products may be considered bioequivalent in extent and rate of absorption if their plasma concentration curves are essentially superimposable.

Oral bioavailability in the context of the present invention is herein defined as the fraction of an orally administered drug that reach the systemic circulation. In practical terms, the oral bioavailability is the percentage of the AUC of a drug available in the blood of a test species after oral administration in relation to the AUC obtained from the same dose administered intravenously to the test subject.

A broad spectrum of methods is available for determining intestinal absorption of compounds in experimental animals. Typical laboratory methods include perfusion via (multiple) lumen tubes, mass balance studies and blood kinetics following oral and intravenous administration of the compound [http://www.rivm.nl/bibliotheek/rapporten/630030001.pdf]. Relevant animal species include mice, rats, dogs, mini pigs and monkey.

Oral bioavailability of a drug and its conjugate can also be predicted to some extend using appropriate in vitro models [Altern. Lab. Anim., 2001, 29, 649-668]. Appropriate in vitro tissue models include everted gut sac, perfused intestinal segments and Ussing chambers. Cell-based in vitro models include small-intestinal cell lines from fetal and neonatal rats and Caco-2 cells.

The term "increasing the oral bioavailability of a drug" or "increased bioavailability" is used herein to indicated that the oral bioavailability of a drug modified according to the invention is increased in comparison to the unmodified drug.

Even a small increase of oral bioavailability can be relevant. E.g. if the drug currently has an oral bioavailability of 30%, an increase to 31 or 32% using the compound of formula (II) of the invention is considered a relevant increase.

For example, a drug with a bioavailability of 30% may form a compound of the invention which, upon oral administration, leads to the accumulation of the unconjugated drug with an oral bioavailability of more than 30%. The increase in oral bioavailability may be in the order of a few percent points, resulting in an increased bioavailability of 31%, 32%, 33%, 34%, 35%, 36%, 37% or even more, such as 38%, 39% or 40% or, even more, such as resulting in an increased bioavailability of 41%, 42%, 43%, 44%, 45%, 46%, 47% or even more such as 48%, 49% or 50%. More spectacular increases have also been observed; depending on the drug and type of monosaccharide, oral bioavailabilities of up to 51%, 52%, 53%, 54%, 55%, 56%, 57% or even more, such as 58%, 59% or 60% or more such as 61%, 62%, 63%, 64%, 65%, 66%, 67% or even more, such as 68%, 69% or 70% appeared achievable. In certain cases the increase was even more, such as 71%, 72%, 73%, 74%, 75%, 76%, 77% or even more such as 78%, 79% or 80%, such as 81%, 82%, 83%, 84%, 85% or above, such as 86%, 87%, 88%, 89% or 90%. In exceptional cases, 91% oral bioavailability may be achieved or more, such as 92%, 93%, 94%, 95%, 96%, 97%, 98%, 99% or even 100%.

The increase of oral bioavailability achieved by the method according to the invention may depend on the drug and type of monosaccharide used. It has been observed that a drug conjugate as prepared using a method according to the invention leads to a higher concentration of the drug (i.e. without the conjugated sugar) in circulation upon oral administration, compared to the concentration of the same unconjugated drug when administered orally.

It was concluded that the human or animal body must have mechanisms to absorb the sugar-linked, N-substituted or unsubstituted carbamoylalkylidene conjugated drug and to remove the sugar-linked, N-substituted or unsubstituted carbamoylalkylidene unit from the drug conjugate.

Without wanting to be bound by theory or by a particular mechanism, the absorption of the afore mentioned drug conjugate may be facilitated by glucose transporters, located at the brushed border of the small intestines, whereas the removal of the glucose moiety may be due to hydrolysis by enzymes (e.g. glycosidases) present in the lining of the small intestines prior to-, or during transport of the drug conjugate from the apical side of the brush border to the blood or, after membrane passage, by hydrolytic enzymes present in the blood or in the liver. Removal of the glucose unit may result in spontaneous hydrolysis of the N-substituted or unsubstituted carbamoyl alkylidene moiety from the drug. For instance, it has been observed in a model system that a glucosidase derived from Aspergillus is able to remove the glucose unit, leading to liberation of the unconjugated drug.

Beside increasing the oral availability of a drug, the compound of formula (II) can also be used to reduce the gastrointestinal side effects of a drug, masking a bad taste of a drug or for the development of a delayed release formulation of a drug. A further embodiment of the compound of formula (II) is to link it to a suitable drug to target tumor tissue.

It has been observed that a compound of formula (I) according to the invention leads to a higher concentration of the drug (i.e. without the conjugated sugar) in circulation upon oral administration, compared to the concentration of the same unconjugated drug.

EXAMPLES

Example 1

Procedure to Prepare O-Linked Drug Conjugates

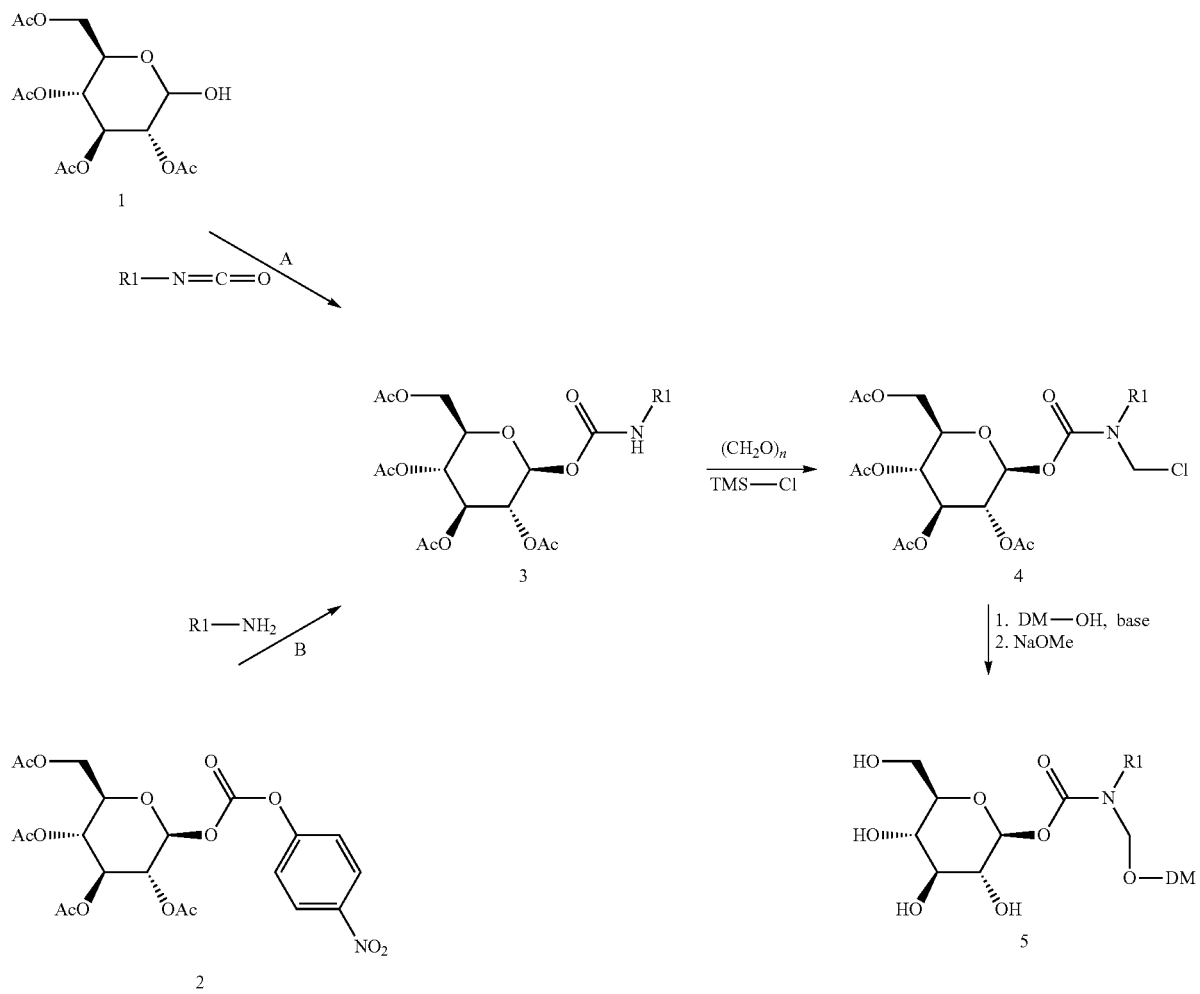

a) R1 = Methyl
b) R1 = Ethyl
c) R1 = Propyl
d) R1 = Butyl
e) R1 = Isopropyl
f) R1 = Cyclopropyl
g) R1 = Cyclobutyl
h) R1 = Cyclopentyl
i) R1 = Cyclohexyl
j) R1 = 4-Pyranyl
k) R1 = 2-Methoxyethyl
l) R1 = Allyl
m) R1 = Carboethoxymethylene
o) R1 = 2-(Methanesulfonyl)ethyl
p) R1 = 3-S-THF
q) R1 = 3-R-THF
r) R1 = Carbomethoxyethyl
s) R1 = 3,3-diflurocyclobutyl
t) R1 = 3-ethoxypropyl
u) R1 = 2-Methylthioethyl Route A The β-linked carbamate intermediates 3 were prepared from known 2,3,4,6-tetra-O-acetyl-D-glucopyranose 1 by reaction with appropriate isocyanates (2 eq) in toluene in the presence of triethylamine for 2-17 h at 20-60° C. until the starting material was completely converted into the carbamate. The reaction mixture was cooled to 15° C. and 3-(dimethylamino)propylamine (1.5 eq) was added. Stirring was continued for 30 min. The reaction mixture was extracted with 2M aq. HCl, water and aq. NaHCO$_3$, dried on magnesium sulfate and evaporated to give the carbamate, which was used without further purification. In a similar fashion, 2,3,4,6-tetra-O-acetyl-β-D-galactopyranosyl, 2,3,4,6-tetra-O-acetyl-α-D-mannopyranosyl and 2,3,4,6,2',3',6'-hepta-O-acetyl-β-D-cellobiosyl carbamates were prepared.

Route B

Carbamate intermediates were obtained by reaction of 1-O-(4-nitrophenoxycarbonyl)-2,3,4,6-tetra-O-acetyl-β-D-glucopyranose 2 and the appropriate amine 1.5 eq. in the presence of triethylamine (2 eq) in dichloromethane for 6-18 h. The reaction mixture was diluted with dichloromethane and extracted with water and aq. NaHCO$_3$, dried on magnesium sulfate and concentrated. The residue was chromatographed on silica gel with an increasing gradient of ethyl acetate in heptane to provide the pure carbamates.

General Procedure for the Preparation of Drug Conjugates from Acetate Protected Glycosyl Carbamates I) Preparation of Methylene Chlorides The chloromethylene building blocks are prepared from the corresponding carbamates 3 by reaction with paraformaldehyde (1.5 eq) and trimethylsilyl chloride (3 eq) in dichloromethane until the reaction mixture becomes clear (2-18 h). Evaporation of the solvents and drying of the residue in vacuo gave the chloromethylene carbamates 4 which were used without further purification.

II) Preparation of Abiraterone Conjugates 7

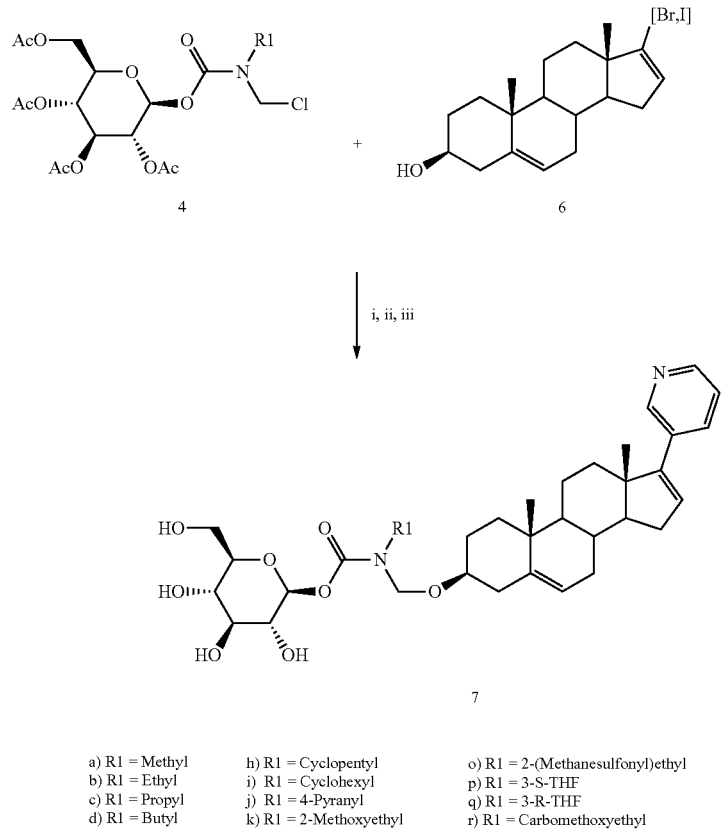

i) DIPEA, RT, 24 h, ii) NaOMe, MeOH; iii) diethyl 3-pyridyl boronate, PPh$_3$, PdCl$_2$(PPh$_3$)$_2$ or Pd(PPh$_3$)$_4$ The chloromethylene derivatives 4 were reacted with either the 17-bromo- or 17-iodo-3β-hydroxy-5α-androstan-5,16-diene 6 in the presence of diisopropylethylamine in dichloromethane for 48 h. The reaction mixture was diluted with dichloromethane, extracted with brine and aq. NaHCO$_3$, dried with magnesium sulfate and concentrated. The residues were purified by flash chromatography with an increasing gradient of ethyl acetate in heptane to give the methylene ethers.

III) Deacetylation

The methylene ethers were dissolved in methanol (10 mL/mM). Sodium methoxide (0.1-1 eq) was added and the reaction mixture was stirred for 1 h at room temperature. The reaction mixture was diluted with ethyl acetate and the reaction mixture was extracted with brine. The organic layer was dried (MgSO$_4$) and evaporated. The residue was dried in vacuo.

IV) Synthesis of 17-pyridyl derivatives from the 3β-substituted 17-bromo-5α-androstan-5,16-diene The 17-bromide (1 eq.), diethyl(3-pyridyl)borane (3 eq.) and triphenylphosphine (0.1 eq.) were dissolved in t-butanol and 2 M sodium carbonate in water. The mixture was degassed with nitrogen and treated with palladium tetrakis(triphenylphosphine) (0.05 eq.) for 3 h at 90° C. Water was added and the mixture was extracted with ethyl acetate. The organic layer was dried with magnesium sulfate and concentrated. The residue was chromatographed on silica gel with an increasing gradient of methanol in dichloromethane to provide the abiraterone conjugates 7.

V) Synthesis of 17-pyridyl derivatives from the 3β-substituted 17-iodo-5α-androstan-5,16-diene The 17-iodide (1 eq.) was dissolved in a 2:1 mixture of THF and MeOH. Diethyl(3-pyridyl)borane (3 eq) was added followed by aq. sodium carbonate (2.00 M, 3 eq). The resulting solution was degassed by bubbling N$_2$ gas through for 30 min. After this time palladium bis(triphenylphosphine) dichloride (0.01 eq) was added and the reaction mixture was stirred at 60° C. for 2 h. Water was added and the aqueous mixture was extracted with ethyl acetate. The organic layer was dried with magnesium sulfate and concentrated. The residue was chromatographed on silica gel with an increasing gradient of methanol in dichloromethane to provide the abiraterone conjugates 7.

17-Iodo-3β-hydroxy-5α-androstan-5,16-diene was reacted with paraformaldehyde (1.5 eq) and trimethylsilyl chloride (3 eq) for 24 h at room temperature. The reaction mixture was concentrated to dryness. The residue was redissolved in DMF and treated with sodium azide (1.2 eq) for 1 h at room temperature. Water was added and the aqueous mixture was extracted with ethyl acetate. The organic layer was extracted with aq NaCl (×3), dried (MgSO4) and concentrated to give a brown solid which was used without further purification. The azide 8 (1 eq) and 1-O-(4-nitrophenoxycarbonyl)-2,3,4,6-tetra-O-acetyl-β-D-glucopyranose 2 (1 eq) was dissolved in dichloromethane. Triphenylphosphine (1 eq) was added and the reaction mixture was stirred for 16 h at room temperature. Triethylamine (3 eq) was added and the reaction mixture was stirred for another 24 h. The reaction mixture was concentrated and chromatographed on silica gel with an increasing gradient of ethyl acetate in heptane to give the methylene ether 9.

Deacetylation and palladium-mediated coupling of the iodide with diethyl(3-pyridyl)borane was accomplished following general procedures III and V to give the unprotected abiraterone conjugate 10.

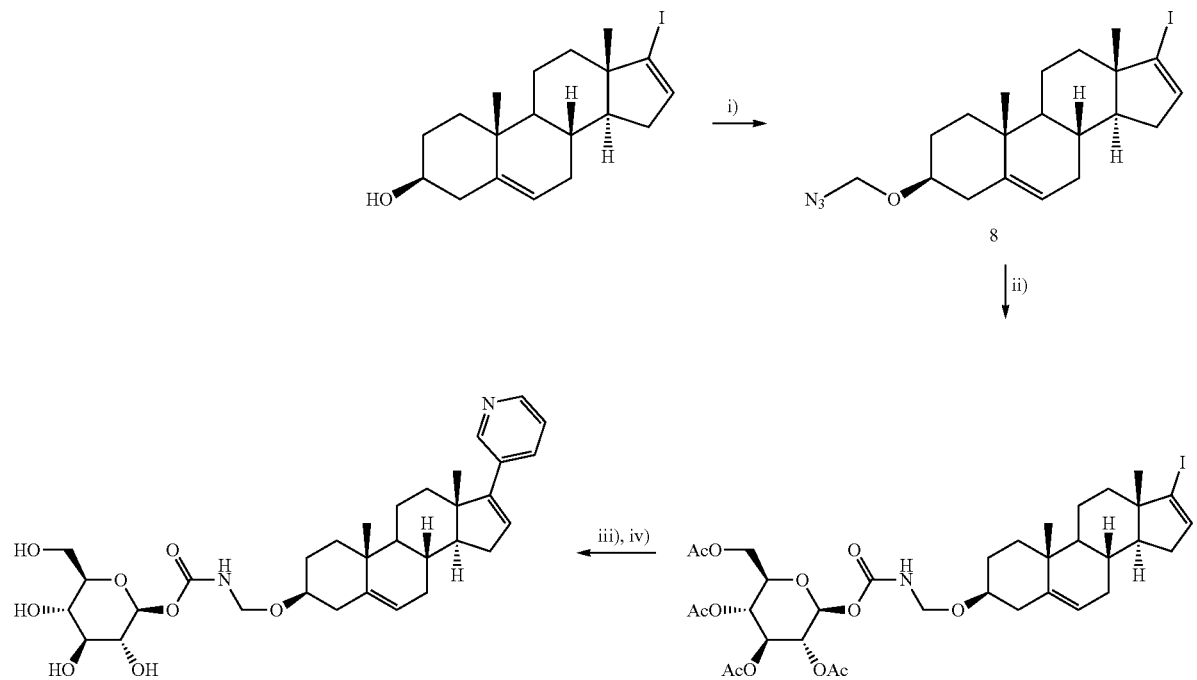

Route C i) 1. (CH$_2$)$_m$ TMSCl; 2. NaN$_3$; ii) 1-O-(4-nitrophenoxycarbonyl)-2,3,4,6-tetra-O-acetyl-β-D-glucopyranose, PPh$_3$; iii) NaOMe, MeOH; iv) diethyl(3-pyridyl)borane, PPh$_3$, Pd(PPh$_3$)$_4$ Route D

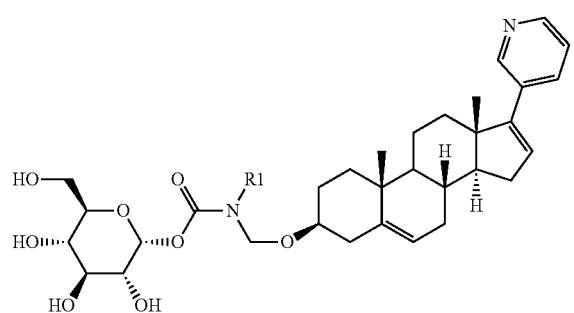

11. R1 = propyl

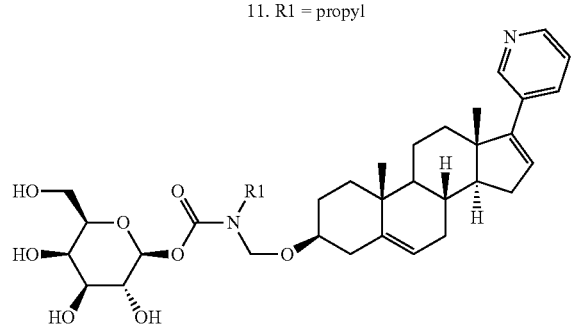

12. R1 = propyl
13. R1 = methyl

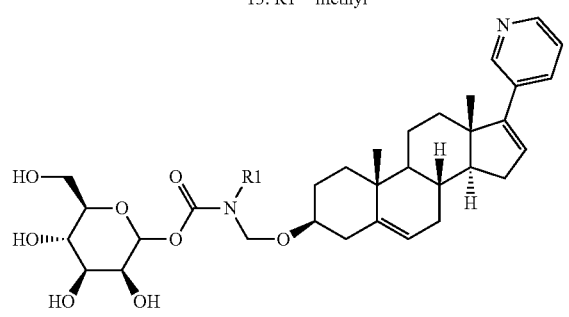

14a. α-isomer, R1 = propyl
14b. β-isomer, R1 = propyl

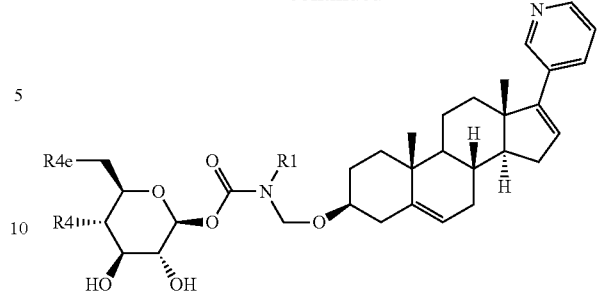

15. R4 = F, R4e = OH, R1 = propyl
16. R4 = OH, R4e = F, R1 = propyl

1-O-(4-Nitrophenoxycarbonyl)-2,3,4,6-tetra-O-acetyl-α-D-glucopyranose [*Bioorg. Med. Chem. Lett.*, 2016, 26, 3774] was reacted with n-propylamine (2 eq.) and triethylamine (2 eq.) in dichloromethane for 5 h. The reaction mixture was diluted with ethyl acetate, extracted with water and aq. NaHCO$_3$. The organic layer was dried (MgSO$_4$) and concentrated. The residue was chromatographed on silica gel with an increasing gradient of ethyl acetate in heptane (0->70%) to give the α-linked n-propylcarbamate. The sequence of reactions to provide the α-linked abiraterone conjugate 11 was identical as described in the General procedure for the preparation of β-linked glucopyranosyl-drug conjugates. Starting from 1-O-p-nitrophenylcarbonyl-2,3,4,6-tetra-O-acetyl-α-D-glucopyranose the unprotected α-linked glucopyranosyl-abiraterone conjugate 11 was obtained.

In a similar fashion as outlined above, unprotected β-linked galactopyranosyl-abiraterone 12 and 13, α- and β-linked mannopyranosyl-abiraterone 14a and 14b, β-linked 4-deoxy-4-fluoro-glucopyranosyl-abiraterone 15 and β-linked 6-deoxy-6-fluoro-glucopyranosyl-abiraterone 16 conjugates could be obtained starting from the corresponding glycosyl n-alkylcarbamates.

The following compounds were prepared with the methods as outlined above:

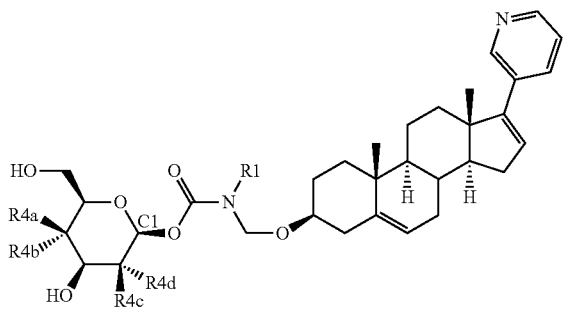

| | R1 | R4c | R4d | R4a | R4b | C1-anomer | Synthesis route | Retention time (min) | Mass [M + H] |
|---|---|---|---|---|---|---|---|---|---|
| 10 | H | OH | H | H | OH | beta | C | 2.84 | 585.4 |
| 7a | Methyl | OH | H | H | OH | beta | B | 2.92 | 599.4 |

-continued

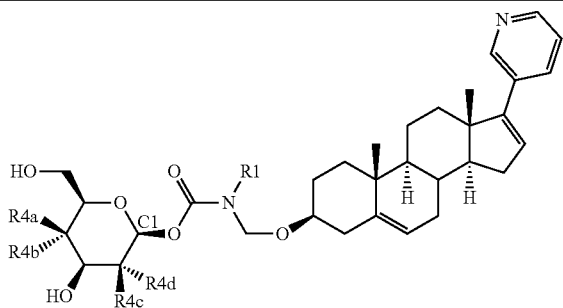

| | R1 | R4c | R4d | R4a | R4b | C1-anomer | Synthesis route | Retention time (min) | Mass [M + H] |
|---|---|---|---|---|---|---|---|---|---|
| 7b | Ethyl | OH | H | H | OH | beta | A | 2.53* | 613.2 |
| 7c | Propyl | OH | H | H | OH | beta | A | 3.18 | 627.6 |
| 7d | Butyl | OH | H | H | OH | beta | A | 3.26 | 641.6 |
| 7e | Isopropyl | OH | H | H | OH | beta | A | 3.15 | 627.6 |
| 7f | Cyclopropyl | OH | H | H | OH | beta | B | 3.01 | 625.6 |
| 7g | Cyclobutyl | OH | H | H | OH | beta | B | 3.17 | 639.6 |
| 7h | Cyclopentyl | OH | H | H | OH | beta | B | 3.30 | 653.6 |
| 7i | Cyclohexyl | OH | H | H | OH | beta | B | 2.80 | 667.2 |
| 7j | 4-Pyranyl | OH | H | H | OH | beta | B | 2.98 | 669.6 |
| 7k | 2-Methoxyethyl | OH | H | H | OH | beta | B | 3.00 | 643.6 |
| 7l | Allyl | OH | H | H | OH | beta | B | 3.12 | 625.4 |
| 7m | Benzyl | OH | H | H | OH | beta | A | 3.28 | 675.6 |
| 7n | Carbethoxymethyl | OH | H | H | OH | beta | A | 3.11 | 671.6 |
| 7o | 2-Methanesulfonylethyl | OH | H | H | OH | beta | B | 2.86 | 691.6 |
| 7p | 3-R-THF | OH | H | H | OH | beta | B | 2.41 | 655.6 |
| 7q | 3-S-THF | OH | H | H | OH | beta | B | 2.11 | 655.5 |
| 7r | Carbomethoxyethyl | OH | H | H | OH | beta | B | 2.54 | 671.6 |
| 7s | 3,3-difluorocyclobutyl | OH | H | H | OH | beta | B | 2.70 | 675.6 |
| 7t | 2-ethoxyethyl | OH | H | H | OH | beta | B | 2.52 | 657.6 |
| 7u | 2-Methylthioethyl | OH | H | H | OH | beta | B | 2.59 | 659.2 |
| 11 | Propyl | OH | H | H | OH | alpha | D | 3.08 | 627.6 |
| 12 | Propyl | OH | H | OH | H | beta | D | 3.10 | 627.6 |
| 13 | Methyl | OH | H | OH | H | beta | D | 2.42 | 599.4 |
| 14a | Propyl | H | OH | H | OH | alpha | D | 3.13 | 627.6 |
| 14b | Propyl | H | OH | H | OH | beta | D | 3.12 | 627.6 |
| 15 | Propyl | OH | H | H | F | beta | D | 2.68 | 629.2 |
| 16 | Propyl (6-F sugar analog) | OH | H | H | OH | beta | D | 2.69 | 629.5 |

UPLC-MS data were recorded on an Agilent 1200 Infinity UPLC system, attached to an Agilent 6100 single quadrupole MS detector. A Kinetex 2.6μ EVO C18 100A column of 50×2.1 mm equipped with a EVO C18 guard column (Phenomenex) was used. The UPLC experiments were run at a flow speed of 0.6 mL/min with a weakly basic solvent system consisting of 10 mM ammonium bicarbonate solution in water (A) and acetonitrile (B). When indicated, a weakly acidic solvent system consisting of 0.1% formic acid in water (A) and acetonitrile containing 0.1% formic acid (B) was used. A gradient was run from 5% B to 60% B in 1.0 minutes, followed by a gradient from 60% to 95% B in 2.0 minutes and keeping the gradient at 95% B for 1 minute.

Example 2

Procedure to Prepare O-Linked Drug Conjugates of Kalydeco

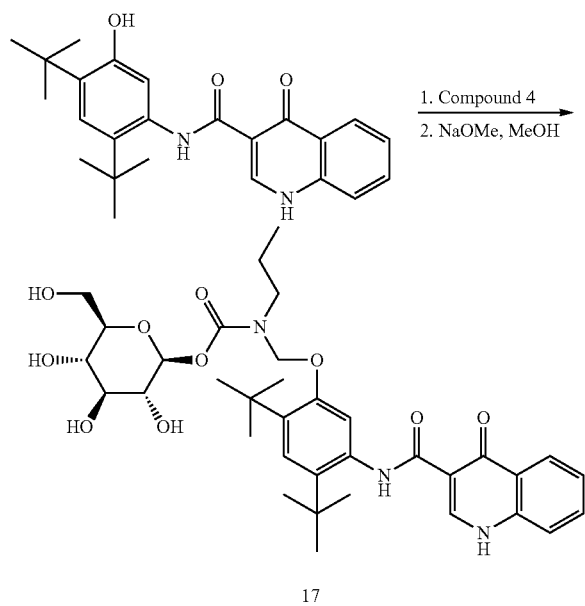

To a suspension of Kalydeco in dichloromethane was added propyl-chloromethyl carbamate 4 (1.1 eq) and N,N-diisopropylethylamine (2 eq). The reaction mixture was stirred for 18 h at room temperature at which time the reaction mixture had become clear. The mixture was concentrated and chromatographed on silica gel with an increasing gradient of ethyl acetate in heptane to give the methylene ether. Deacetylation was performed by dissolving the methylene ether in a 1:2 mixture of dioxane and methanol, followed by the addition of a catalytic amount of sodium methoxide. The reaction mixture was stirred for 2 h. Water was added and the resulting mixture was extracted with ethyl acetate. The organic layer was dried ($MgSO_4$) and concentrated. The residue was chromatographed on silica gel with an increasing gradient of methanol in dichloromethane to give the unprotected glucose-Kalydeco conjugate 17. UPLC-MS: retention time 3.06 min; Mass found 670.2 [M+H] (formic acid solvent system).

Example 3

Procedure to Prepare O-Linked Drug Conjugates of Gemcitabine

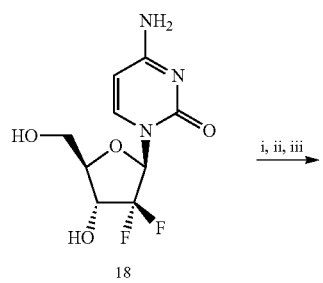

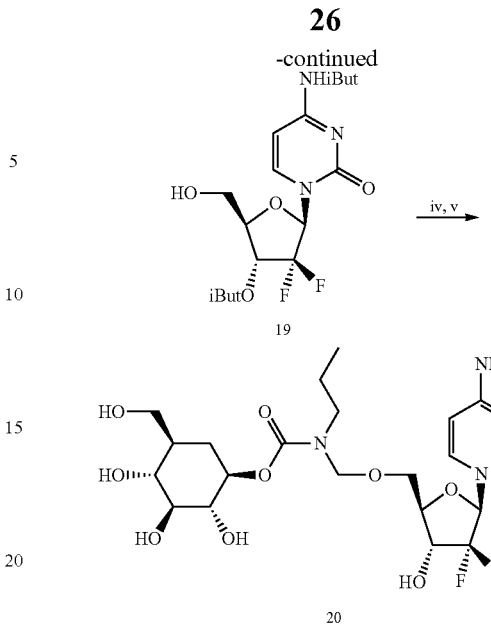

i) TBDMS-Cl, pyridine; ii) isobutyryl chloride, pyridine; iii) pTsOH, $CH_3CN$, $H_2O$; iv) 4c, DIPEA; v) 1. NaOMe, MeOH; 2. conc. $NH_4OH$, 50° C.

Gemcitabine was reacted with TBDMS-Cl (1.2 eq) in pyridine for 3 h. Water was added and the reaction mixture was concentrated. The residue was taken up in ethyl acetate and extracted with water and aq. $NaHCO_3$, dried ($MgSO_4$) and concentrated. The residue was dissolved in pyridine and isobutyryl chloride (2.2 eq) was added. The resulting mixture was stirred for 66 h at room temperature. Water was added and the reaction mixture was concentrated. The residue was taken up in ethyl acetate and extracted with water and aq. $NaHCO_3$, dried ($MgSO_4$) and concentrated and coevaporated twice with toluene. The residue was chromatographed on silica gel and eluted with an increasing gradient of methanol in dichloromethane. The pure fractions were collected and evaporated to dryness. The product obtained was dissolved in acetonitrile. 10% v/v water was added. Then, p-toluene sulfonic acid monohydrate (3 eq) was added and the reaction mixture was stirred for 66 h at room temperature. The mixture was diluted with ethyl acetate, extracted with water and aq. $NaHCO_3$, dried ($MgSO_4$) and concentrated. The residue was chromatographed on silica gel with an increasing gradient of methanol in dichloromethane to give the 5-OH unprotected gemcitabine derivative.

This compound was reacted with the propyl-chloromethyl carbamate 4 (2 eq) in the presence of N,N-diisopropyethylamine (6 eq) for 72 h at room temperature. Water was added and the mixture was extracted with dichloromethane. The organic layer was dried ($MgSO_4$) and concentrated. The residue was chromatographed on silica gel and eluted with an increasing gradient of methanol in dichloromethane to give the methylene ether. Deacetylation was performed by dissolving the methylene ether in a 1:2 mixture of dioxane and methanol, followed by the addition of a catalytic amount of sodium methoxide. The reaction mixture was stirred for 2 h. Water was added and the resulting mixture was extracted with ethyl acetate. The organic layer was dried ($MgSO_4$) and concentrated. The residue was chromatographed on silica gel with an increasing gradient of methanol in dichloromethane to give the unprotected gemcitabine conjugate 20. UPLC-MS: retention time 0.327 min; Mass found 541.1 [M+H] (formic acid solvent system).

Example 4

Procedure to Prepare O-Linked Drug Conjugates of Niclosamide

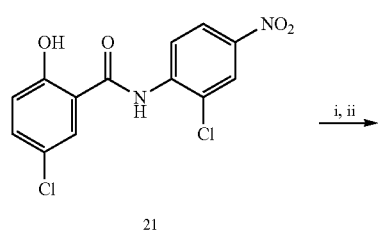

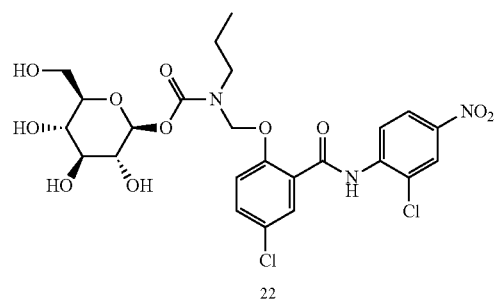

i) 4c, DIPEA; ii) NaOMe, MeOH

Niclosamide 21 and propyl chloromethyl-carbamate 4 (1.3 eq) were suspended in dichloromethane. N,N-diisopropylethylamine (5 eq) was added and the reaction mixture was stirred for 16 h. The mixture was concentrated and chromatographed on silica gel with an increasing gradient of ethyl acetate in heptane. The pure fractions were concentrated and dried in vacuo. The acetylated product was dissolved in a 1:1 mixture of THF and methanol. Sodium methoxide (1 eq) was added and the reaction mixture was stirred for 1 h. Water was added and the reaction mixture was extracted with ethyl acetate. The organic layer was dried ($MgSO_4$) and concentrated. The residue was chromatographed on silica gel and eluted with an increasing gradient of methanol in dichloromethane to give the unprotected niclosamide conjugate 22. UPLC-MS: retention time 2.97 min (ES-API); Mass found (M+Na) 627.0 (formic acid solvent system).

Example 5

Procedure to Prepare O-Linked Drug Conjugates of Dihydroartemisinin

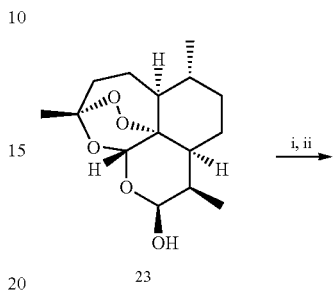

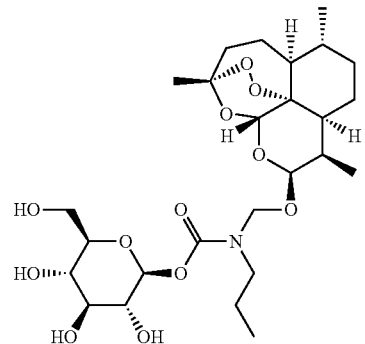

i) 4c, DIPEA; ii) NaOMe, MeOH

To a solution of dihydroartemisinin 23 and propyl chloromethyl carbamate chloride 4 (2 eq) in dichloromethane was added N,N-diisopropylethylamine (5 eq) and the mixture was stirred at RT for 48 h. The reaction mixture was concentrated and chromatographed on silica gel with an increasing gradient of ethyl acetate in heptane. The pure fractions were combined and concentrated to dryness. The obtained material was dissolved in a 1:1 mixture of THF and methanol. Sodium methoxide (1 eq) was added and the reaction mixture was stirred for 1 h. Water was added and the mixture was extracted with ethyl acetate. The organic layer was dried ($MgSO_4$) and concentrated. The residue was chromatographed on silica gel with an increasing gradient of methanol in dichloromethane to give the unprotected dihydroartemisinin conjugate 24. UPLC-MS: retention time 2.77 min (ES-API); [M+Na] 585.2 (formic acid solvent system).

Example 6

Procedure to Prepare 3-O-Linked Drug Conjugate 26 of Fulvestrant

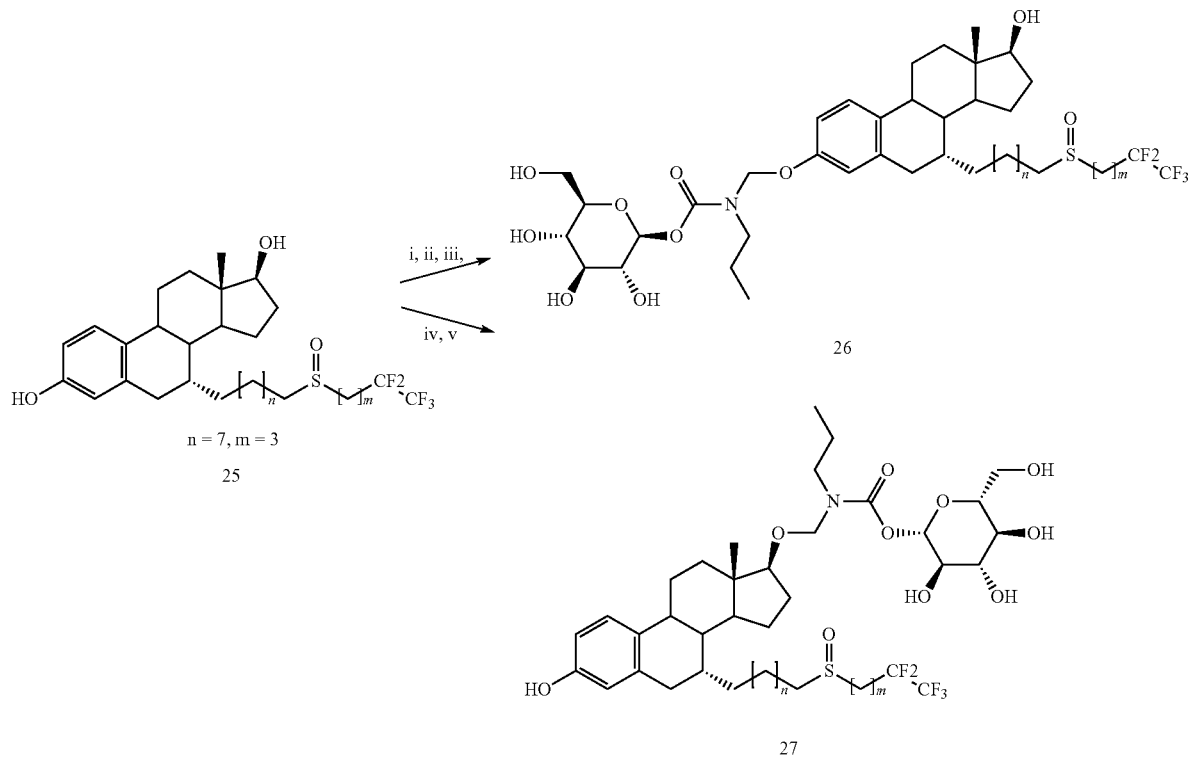

i, HCOOEt, reflux; ii) 4c, DIPEA; iii) NaOMe, MeOH; iv) BzCl; v) 4c, DIPEA; vi) NaOMe, MeOH Fulvestrant-17-O-formate was prepared from Fulvestrant 25 as reported [*J. Chem. Soc., Perkin Trans.* 1, 2001, 3037]. To a solution of Fulvestrant-17-O-formate (750 mg, 1.18 mmol) in methylene chloride (5 mL) was added DIPEA (1.01 mL) and the reaction mixture was stirred for 18 h. The reaction mixture was concentrated and chromatographed on silica gel with an increasing gradient of ethyl acetate in heptane. The pure fractions were combined and concentrated to dryness. The obtained material was dissolved in a 1:1 mixture of THF and methanol. Sodium methoxide (1 eq) was added and the reaction mixture was stirred for 1 h. Water was added and the mixture was extracted with ethyl acetate. The organic layer was dried (MgSO4) and concentrated. The residue was chromatographed on silica gel with an increasing gradient of methanol in dichloromethane to give the unprotected Fulvestrant conjugate 26. UPLC-MS: retention time 3.23 min (ES-API) Mass found (M+Na) 907.6 (formic acid solvent system).

Example 7

Procedure to Prepare 17-O-Linked Drug Conjugate 27 of Fulvestrant

3-O-Benzoyl-Fulvestrant was prepared as reported [*J. Chem. Soc., Perkin Trans.* 1, 2001, 3037] and was dissolved in dichloromethane. The propyl-chloromethyl carbamate derivative 4 (1.3 eq) and DIPEA (5 eq) were added and the reaction mixture was stirred for 72 h at room temperature. The reaction mixture was concentrated and chromatographed on silica gel with an increasing gradient of ethyl acetate in heptane to give the protected Fulvestrant conjugate. The obtained product was dissolved in a 1:1 mixture of THF and methanol. Sodium methoxide (1 eq) was added and the mixture was stirred for 1 h. Water was added and the mixture was extracted with ethyl acetate. The organic layer was dried (MgSO4) and concentrated. The residue was chromatographed on silica gel with an increasing gradient of methanol in dichloromethane to give the unprotected Fulvestrant conjugate 27. UPLC-MS: retention time 3.29 min (ES-API) Mass found (M+Na) 907.6 (formic acid solvent system).

Example 8

Procedure to Prepare O-Linked Drug Rotigotine Conjugate 28

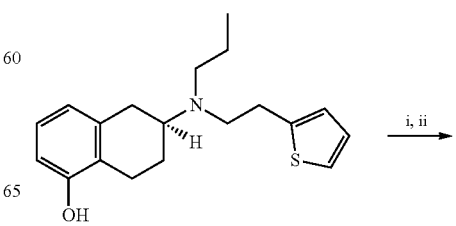

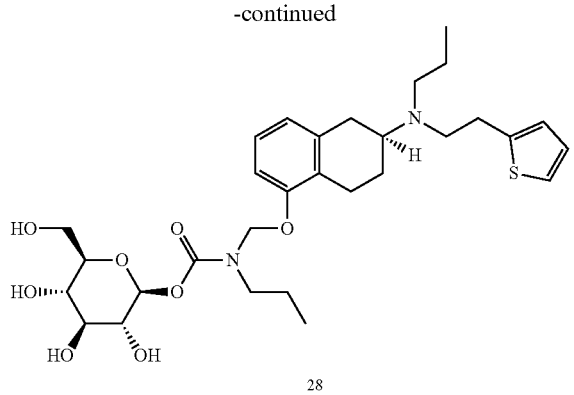

28 i) 4, DIPEA; ii) NaOMe, MeOH

To a solution of Rotigotine (2 mM) and propyl chloromethyl carbamate 4 (2 mM) in dichloromethane was added N,N-diisopropylethylamine (3 eq) and the mixture was stirred at RT for 24 h. The reaction mixture was concentrated and chromatographed on silica gel with an increasing gradient of ethyl acetate in heptane. The pure fractions were combined and concentrated to dryness. The obtained material was dissolved in a 1:1 mixture of THF and methanol. Sodium methoxide (1 eq) was added and the reaction mixture was stirred for 1 h. Aqueous ammonium chloride (1 M) was added and the mixture was extracted with ethyl acetate. The organic layer was dried (MgSO$_4$) and concentrated. The residue was chromatographed on silica gel with an increasing gradient of methanol in dichloromethane to give the unprotected Rotigotine conjugate 28 (374 mg). UPLC-MS: retention time 4.46 min (ES-API); [M+H] 593.2 (formic acid solvent system).

Example 9

Procedure to Prepare O-Linked Drug Edavarone Conjugate 29

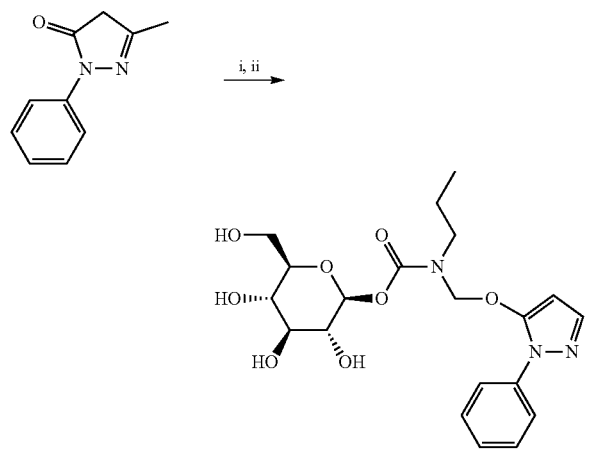

29 i) Cs$_2$CO$_3$, 4; ii) NaOMe, MeOH 5-methyl-2-phenyl-4H-pyrazol-3-one (2.54 mmol) and cesium carbonate (2.54 mmol) were stirred in acetone (10.0 mL) for 1 h. After this time chloromethyl propyl carbamate 4 in acetone (5 mL) was added. The resulting solution was stirred for 24 h. After this time the solution was filtered and concentrated. The residue was chromatographed on silica gel with an increasing gradient of ethyl acetate in heptane to give the protected Edavarone conjugate (460 mg). To a solution of the protected conjugate in MeOH (5 mL) was added sodium methoxide (68.9 mg, 1.27 mmol) and the solution stirred at RT until no starting material remained. After this time the solution was diluted with EtOAc (100 mL), washed with sodium bicarbonate solution, dried (MgSO4) and concentrated. The residue was chromatographed on silica gel with an increasing gradient of methanol in dichloromethane to give the unprotected Edavarone conjugate 29 (274 mg). UPLC-MS: retention time 4.37 min (ES-API); [M+H] 452.2 (formic acid solvent system).

Example 10

Procedure to Prepare O-Linked Drug Conjugate 30 of Cannabidiol

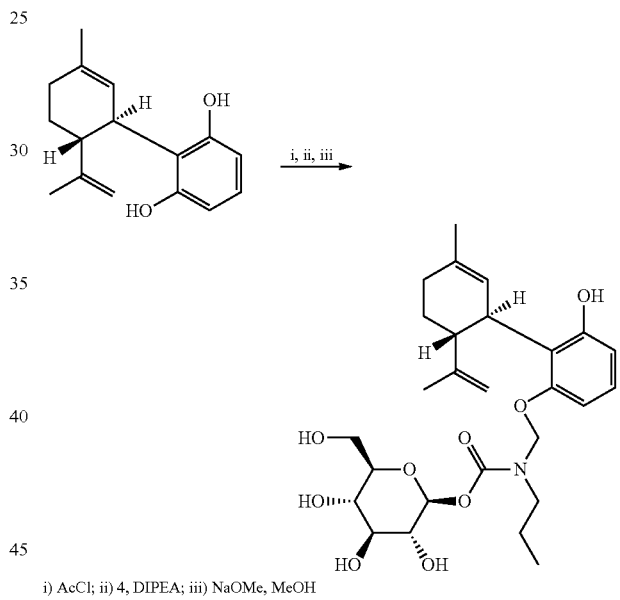

i) AcCl; ii) 4, DIPEA; iii) NaOMe, MeOH

To a solution of Cannabidiol in THF was added triethylamine (1.24 mL) followed by acetyl chloride (559 mg). The resulting solution was stirred for 2 h at RT. Water was added and the aqueous layer extracted with methylene chloride. The organic layers were dried and concentrated to give an oil which was purified by flash chromatography to give a mixture of mono- and diacetylated cannabidiol mono- and diacetate (1200 mg) which was used without further purification.

To a solution of the mono- and diacetate mixture from the previous experiment (600 mg) in acetone (10.0 mL) and K$_2$CO$_3$ (698 mg) was added, followed by a solution of chloromethylpropyl carbamate 4 (811 mg) in acetone (10 mL). The resulting solution was stirred until no further reaction observed by LCMS. After this time the solution was filtered and concentrated. The residue was dissolved in DCM and then purified by flash chromatography to give the protected cannabidiol conjugate (480 mg).

To a solution of the protected cannabidiol conjugate (480 mg) in MeOH (10 mL) was added sodium methoxide (32 mg) and the solution stirred at room temperature for 2 h. After this time saturated aq. ammonium chloride was added and the water layer was extracted with ethyl acetate, dried and concentrated. The residue was chromatographed on silica gel with an increasing gradient of methanol in dichloromethane to give the unprotected cannabidiol conjugate 30 (274 mg). UPLC-MS: retention time 3.04 min (ES-API); [M+H] 614.4 (formic acid solvent system). (328 mg).

Example 11

Determination of Oral Bioavailability of Abiraterone Conjugates

Relative and absolute bioavailability may be determined in different animal models and according to different protocols. The following protocol is typical for determining bioavailability in female Beagle dogs. The animals were deprived from food over a time period of 8 h prior to administration and 2 h after administration of the test molecules. Water was supplied without limitation.

On the study day, the animals received test molecules, at a single dose of 15 μmole/kg, by oral gavage, formulated in mixtures of propylene glycol, ethanol and 0.9% NaCl+5% mannitol in water. Blood samples were collected from the jugular vein on the following time points: 0.25, 0.5, 1, 2, 4, 8 and 24 hours after dosing.

Circulating concentrations of test compounds were determined over a time period of 24 h using LC/MS/MS methods with demonstrated specificity and error over a concentration range of 1.0 ng/mL (LLQ) to 2500 ng/mL (1 day validation).

Pharmacokinetic parameters were calculated from concentration versus time data using non-compartmental pharmacokinetic methods using Phoenix pharmacokinetic software. Data are compared to Zytiga to establish improvement of its oral bioavailability by the Abiraterone conjugates.

| Compound | AUC$_{last}$ | Conversion rate to Abiraterone |
|---|---|---|
| 3-O-Acetate (Zytiga) (comparative) | o | nd |
| 3-O-β-Glucoside (33) (comparative) | + | + |
| 7a | ++ | +++ |
| 7b | + | ++++ |
| 7c | ++ | +++ |
| 7g | ++ | ++ |
| 7j | ++ | ++ |
| 7k | + | ++++ |
| 7l | ++ | +++ |
| 7s | + | ++++ |
| 13 | ++ | ++ |

AUC$_{last}$ (total amount abiraterone and conjugate)
o AUC$_{last}$ value for Zytiga
+ 1.1-6-fold increase compared to Zytiga
++ >7-fold increase compared to Zytiga
Conversion rate: AUC$_{last}$ Abiraterone/AUC$_{last}$ conjugate + AUC$_{last}$ Abiraterone × 100%
nd = not determined
+ 1-20%
++ 21-40%
+++ 41-50%
++++ >51%

3-O-β-D-Glucopyranosyl-abiraterone 33 was obtained according to the following scheme:

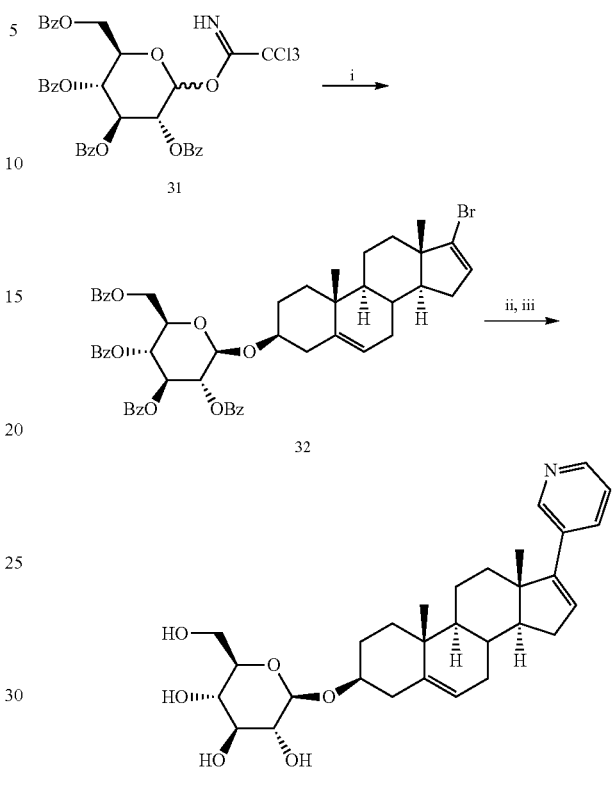

i) BF$_3$·Et$_2$O; NaOMe, MeOH;, iii) diethyl(3-pyridyl)borane, PPh$_3$, Pd(PPh$_3$)$_4$, Na$_2$CO$_3$ Known 31 was reacted with 17-bromo-3β-hydroxy-5α-androstan-5,16-diene 6 in the presence of boron trifluoride etherate to give the glucoside 32. Compound 32 was debenzoylated with sodium methoxide in methanol, followed by reaction with diethyl(3-pyridyl)borane in the presence of triphenylphosphine, palladium tetrakistriphenylphosphine and sodium carbonate to give the unprotected glucoside 33.

Example 12

Determination of Oral Bioavailability of Kalydeco Conjugates

In a similar fashion as described in Example 11, the bioavailability increase of Kalydeco conjugate 17 was determined.

| Compound | AUC$_{last}$ | Conversion rate to Kalydeco |
|---|---|---|
| Kalydeco | o | |
| 17 | + | ++++ |

AUC$_{last}$ (total amount Kalydeco and conjugate)
o AUC$_{last}$ value for Kalydeco
+ 1.1-6-fold increase compared to Kalydeco
Conversion rate: AUC$_{last}$ Kalydeco/AUC$_{last}$ conjugate + AUC$_{last}$ Kalydeco × 100%
nd = not determined
+ 1-20%
++ 21-40%
+++ 41-50%
++++ >51%

Example 13

Determination of Oral Bioavailability of Fulvestrant Conjugates

In a similar fashion as described in Example 11, the bioavailability increase of Fulvestrant conjugate 26 was determined.

| Compound | AUC$_{last}$ | Conversion rate to Fulvestrant |
| --- | --- | --- |
| Fulvestrant | o | |
| 26 | + | ++++ |

AUC$_{last}$ (total amount Fulvestrant and conjugate)
o AUC$_{last}$ value for Fulvestrant
+ 1.1-6-fold increase compared to Fulvestrant
Conversion rate: AUC$_{last}$ conjugate/AUC$_{last}$ conjugate + AUC$_{last}$ Fulvestrant × 100%
nd = not determined
+ 1-20%
++ 21-40%
+++ 41-50%
++++ >51%

Example 14

Determination of Oral Bioavailability of Rotigotine Conjugate

In a similar fashion as described in Example 11, the bioavailability increase of Rotigotine conjugate 28 was determined.

| Compound | AUC$_{last}$ | Conversion rate to Rotigotine |
| --- | --- | --- |
| Rotigotine | o | |
| 28 | ++ | ++++ |

AUC$_{last}$ (total amount Rotigotine and conjugate)
o AUC$_{last}$ value for Rotigotine
++ >6-fold increase compared to Rotigotine
Conversion rate: AUC$_{last}$ conjugate/AUC$_{last}$ conjugate + AUC$_{last}$ Rotigotine × 100%
nd = not determined
+ 1-20%
++ 21-40%
+++ 41-50%
++++ >51%

The above examples teach that O-glucosides of drugs, such as Abiraterone and Kalydeco did not show an increase in oral bioavailability in comparison to the parent drug. Moreover, both glucosides showed very slow hydrolysis into the parent drugs.

Without wishing to be bound by any theory, it is believed that the results of the present invention are based on the use of linker moieties to improve the uptake and to achieve a more predictable hydrolysis rate of the drug glycosides. These linker moieties are positioned between the anomeric hydroxyl of the sugar residue and the drug and serve as molecular interface that create a certain distance between the sugar and drug moieties which may facilitate absorption and improve the interaction with an appropriate glycosidase. A self-immolative linker could prevent accumulation of intermediates.

In a comparative experiment (results not shown) several self-immolative linkers such as diaminoethyl linker conjugates of Kalydeco and Abiraterone were prepared. Enzymatic removal of the glucose moiety of those conjugates did not result in formation of Kalydeco or Abiraterone, respectively. Rather, the intermediate aminoethyl conjugates were observed.

Similar results were obtained with the glutathione-sensitive disulfanylethyl glycoconjugate of Abiraterone. Cleavage of the disulfide bond with glutathione did not produce significant amounts of Abiraterone, but rather produced the mercaptoethyl conjugate as well as various adducts. In contrast, compounds such as 7c, 7k and 17 were readily converted to Abiraterone and Kalydeco, respectively, upon treatment with β-glucosidase.

These results indicate that while physicochemical characteristics of a drug can be improved by converting a drug into a drug-glycoside, significant improvement of oral bioavailability with this type of prodrug is not always achieved, contrary to the results of the invention as shown above.

What is claimed is:
1. A compound of formula (I)

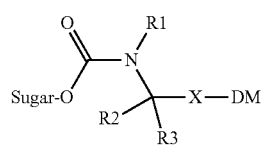

Formula (I)

wherein Sugar is a beta-linked monosaccharide,
wherein the Sugar is glucose or galactose,
wherein optionally one or more OH groups are replaced by a group R4;
  wherein R4 is selected from the group consisting of $C_1$-$C_6$ alkoxy, chlorine, fluorine, cyano, $CF_3$, $NH_2$, $C_1$-$C_6$ alkyl-NH, $C_1$-$C_6$ dialkyl-N, $C_1$-$C_6$ cycloalkyl-N, $C_1$-$C_6$ alkyl-C(O)NH, $C_1$-$C_6$ alkyl-C(O)($C_1$-$C_6$ alkyl)-N, HC(O)($C_1$-$C_6$ alkyl)-N, $C_1$-$C_6$ alkyl-O—C(O)NH, $C_1$-$C_6$ alkyl-O—C(O)($C_1$-$C_6$ alkyl)-N, and $C_1$-$C_6$ alkyl-O—C(O)—O;
R1 is selected from the group consisting of H, $C_1$-$CH_6$ alkyl, $C_2$-$CH_6$ alkenyl, $C_2$-$C_6$ alkynyl, —R5—O—R7, —R5—S—R7, —R6—C(O)—R7, —R6—C(O)—O—R7, —R5—SO$_2$—R7, —R5—SO$_2$—NR7R8, $C_3$$C_7$ cycloalkyl, $C_4$-$C_7$ cycloalkenyl, a 4 to 7 membered heterocycle, aryl and ($C_1$-$C_3$ alkyl)-aryl;
wherein R5 is $C_2$ or $C_3$ alkyl, R6 is $C_1$-$C_3$ alkyl, R7 and R8 are independently hydrogen or $C_1$-$C_3$-alkyl;
and wherein the $C_3$-$C_7$ cycloalkyl, $C_4$-$C_7$ cycloalkenyl, a 4 to 7 membered heterocycle, aryl and ($C_1$-$C_3$alkyl)-aryl groups can be optionally substituted by R9,
wherein R9 is selected from the group consisting of $C_1$-$C_4$ alkyl, $C_1$-$C_4$ alkoxy, chlorine, fluorine, cyano, $CF_3$, amine, amide, carbamate and —C(O)O—($C_1$-$C_4$-alkyl);
R2 and R3 are both H, or one of R2 and R3 is H and the other is $C_1$-$C_6$ alkyl;
X-DM represents a drug moiety wherein X is O or S;
or a pharmaceutically acceptable salt thereof.
2. The compound according to claim 1, wherein R1 is selected from the group consisting of $C_1$-$C_4$ alkyl, $C_2$-$C_4$ alkenyl, —R5—O—R7, —R5—S—R7, —R6—C(O)—R7, —R6—C(O)—O—R7, —R5—SO$_2$—R7, —R5—SO$_2$—NR7R8, $C_3$-$C_7$ cycloalkyl, wherein $C_3$-$C_7$ cycloalkyl is optionally substituted by one or two fluorine; pyranyl, tetrahydrofuranyl and benzyl, wherein R5 is $C_2$ or $C_3$ alkyl, R6 is $C_1$-$C_3$ alkyl, R7 and R8 are independently hydrogen or $C_1$-$C_3$-alkyl.

3. The compound according to claim 2, wherein R1 is selected from the group consisting of $C_1$-$C_4$ alkyl, allyl, methoxyethyl, ethoxyethyl, methylthioethyl, $C_3$-$C_6$ cycloalkyl, wherein the $C_3$-$C_6$ cycloalkyl can be optionally substituted by one or two F, pyranyl, tetrahydrofuranyl, benzyl, carbethoxymethyl, carbomethoxyethyl and methanesulfonyl ethyl.

4. The method according to claim 1, wherein the compound has the structure

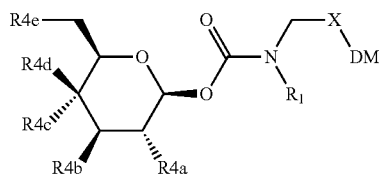

wherein R1, X and DM are as defined above and R4a, R4b, R4c, R4d and R4e are independently selected from OH, F and H with the following provisions: at least two of R4a, R4b, R4c, R4d and R4e are OH whereas R4c and R4d cannot both be OH.

5. The method according to any one of the preceding claims wherein R2 and R3 are both H.

6. The method according to any one of the preceding claims, wherein the drug moiety is selected from the group consisting of quetiapine, montelukast, venlafaxine, mesalazine, desvenlafaxine, metoprolol, paliperidone, buprenorphine, morphine, ganciclovir, tapentadol, rotigotine, abiraterone, acetaminophen, saxagliptin, fulvestrant, afimoxifene, testosterone, simvastatin, tolterodine, tramadol, atenolol, naloxone, nabilone, metaraminol, dihydroartemisinin, orciprenaline, labetalol, kalydeco, azacitidine, niclosamide, tetrahydrocannabinol, raloxifene, propofol, gemcitabine, cannabidiol, carvedilol, edavarone, cytarabine, dasatinib, perrilyl alcohol, butorphanol and bazedoxifene.

7. Pharmaceutical composition comprising a compound according to claim 1 and a pharmaceutically acceptable carrier.

8. A method for increasing the oral bioavailability of a drug HX-DM. wherein HX represents an OH or SH functional group, comprising the step of linking a sugar-carbamoylalkylidene unit of formula (II)

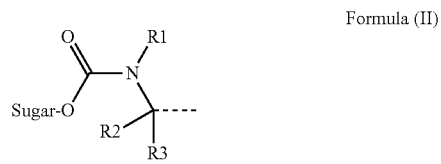

Formula (II)

wherein Sugar, R1, R2 and R3 are as defined in claim 1 and wherein—represents a leaving group,
to the OH or SH functional group of the drug HX-DM in order to obtain a compound according to formula (I)

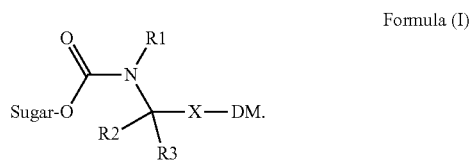

Formula (I)

* * * * *

UNITED STATES PATENT AND TRADEMARK OFFICE
CERTIFICATE OF CORRECTION

PATENT NO. : 11,633,484 B2
APPLICATION NO. : 16/956172
DATED : April 25, 2023
INVENTOR(S) : Somhairle Mac Cormick and Gerrit Herman Veeneman It is certified that error appears in the above-identified patent and that said Letters Patent is hereby corrected as shown below:

In the Claims

Column 36, Claim 1, Line 44-47 reads:
R1 is selected from the group consisting of H, C1-CH6
alkyl, C2-CH6 alkenyl, C2-C6 alkynyl, —R5—O—R7,
—R5—S—R7, —R6—C(O)—R7, —R6—C(O)—
O—R7, —R5—SO2—R7, —R5—SO2—NR7R8,
C3C7 cycloalkyl, C4-C7 cycloalkenyl, a 4 to 7 mem-
Whereas it should read:
R1 is selected from the group consisting of C1-C6
alkyl, C2-C6 alkenyl, C2-C6 alkynyl, -R5-O-R7,
-R5-S-R7, -R6-C(O)-R7, -R6-C(O)-
O-R7, -R5-SO2-R7, -R5-SO2-NR7R8,
C3-C7 cycloalkyl, C4-C7 cycloalkenyl, a 4 to 7 mem- Column 37, Claim 4, Line 11 reads:
4. The method according to claim 1, wherein the com-
Whereas it should read:
4. The compound according to claim 1, wherein the com- Column 37, Claim 5, Line 28-29 reads:
5. The method according to any one of the preceding
claims wherein R2 and R3 are both H.
Whereas it should read:
5. The compound according to claim 1, wherein R2 and R3 are both H.

Column 37, Claim 6, Line 30-31 reads:
6. The method according to any one of the preceding
claims, wherein the drug moiety is selected from the group Signed and Sealed this
Twenty-seventh Day of June, 2023

Katherine Kelly Vidal
*Director of the United States Patent and Trademark Office*

CERTIFICATE OF CORRECTION (continued)
U.S. Pat. No. 11,633,484 B2

Whereas it should read:
6. The compound according to claim 1,
wherein the drug moiety is selected from the group